(12) United States Patent
Squicciarini

(10) Patent No.: US 8,360,956 B2
(45) Date of Patent: Jan. 29, 2013

(54) THERAPEUTIC PROSTHETIC DEVICE

(75) Inventor: John B Squicciarini, Aliso Viejo, CA (US)

(73) Assignee: EPD Scientific, Huntington Beach, CA (US)

( * ) Notice: Subject to any disclaimer, the term of this patent is extended or adjusted under 35 U.S.C. 154(b) by 953 days.

(21) Appl. No.: 12/403,297

(22) Filed: Mar. 12, 2009

(65) Prior Publication Data

US 2009/0171144 A1    Jul. 2, 2009

Related U.S. Application Data

(63) Continuation-in-part of application No. 11/938,661, filed on Nov. 12, 2007, now Pat. No. 7,527,589, which is a continuation-in-part of application No. 11/733,347, filed on Apr. 10, 2007, now Pat. No. 7,503,892, application No. 12/403,297, which is a continuation-in-part of application No. 11/733,347.

(60) Provisional application No. 60/791,149, filed on Apr. 10, 2006.

(51) Int. Cl.
*A61F 5/00* (2006.01)

(52) U.S. Cl. .......................................... 600/38

(58) Field of Classification Search ................ 128/842, 128/844, 845; 600/38–41
See application file for complete search history.

(56) References Cited

U.S. PATENT DOCUMENTS

| | | |
|---|---|---|
| 4,671,262 A | 6/1987 | West |
| 4,690,135 A | 9/1987 | Gerow |
| 5,076,287 A | 12/1991 | Johnson |
| 5,137,032 A | 8/1992 | Harmon |
| 5,201,327 A | 4/1993 | Johnson |
| 5,413,611 A | 5/1995 | Haslam, II et al. |
| 5,823,939 A | 10/1998 | Tsagarakis |
| 5,984,880 A | 11/1999 | Lander et al. |
| 6,246,915 B1 | 6/2001 | Boutos |
| 6,266,560 B1 | 7/2001 | Zhang et al. |
| 6,350,230 B1 | 2/2002 | Kontos |
| 6,547,717 B1 | 4/2003 | Green et al. |
| 6,599,236 B1 | 7/2003 | Castro |
| 6,695,770 B1 | 2/2004 | Choy et al. |
| 6,749,558 B1 | 6/2004 | Brintle |
| 6,814,695 B1 | 11/2004 | Wyllie et al. |
| 7,104,950 B2 | 9/2006 | Levy |
| 7,186,212 B1 | 3/2007 | McMullen |
| 2003/0036678 A1 * | 2/2003 | Abbassi .......................... 600/38 |
| 2004/0082831 A1 | 4/2004 | Kobashikawa et al. |
| 2006/0189949 A1 | 8/2006 | Tomosada et al. |
| 2006/0270897 A1 | 11/2006 | Homer |
| 2007/0238918 A1 | 10/2007 | Squicciarini |
| 2008/0065187 A1 | 3/2008 | Squicciarini |

\* cited by examiner

*Primary Examiner* — Samuel Gilbert
(74) *Attorney, Agent, or Firm* — Haynes and Boone, LLP

(57) ABSTRACT

A therapeutic prosthetic device for women or men configured to transmit tactile sensations through a stimulation material to the surface of a sex organ such as the vagina or penis. The therapeutic prosthetic device can include sensors and stimulators on the outer surface and inner surface and a controller. Sensors for detecting state, sensation or movement can be disposed within, on, or separate from the device and can transmit signals electrically or wirelessly to a microprocessor, which is programmed to generate stimulation sensations in response to signals from the sensors, stimulation materials, or controllers that are transmitted to the stimulation material. In one embodiment the therapeutic prosthetic device is a therapeutic condom.

8 Claims, 10 Drawing Sheets

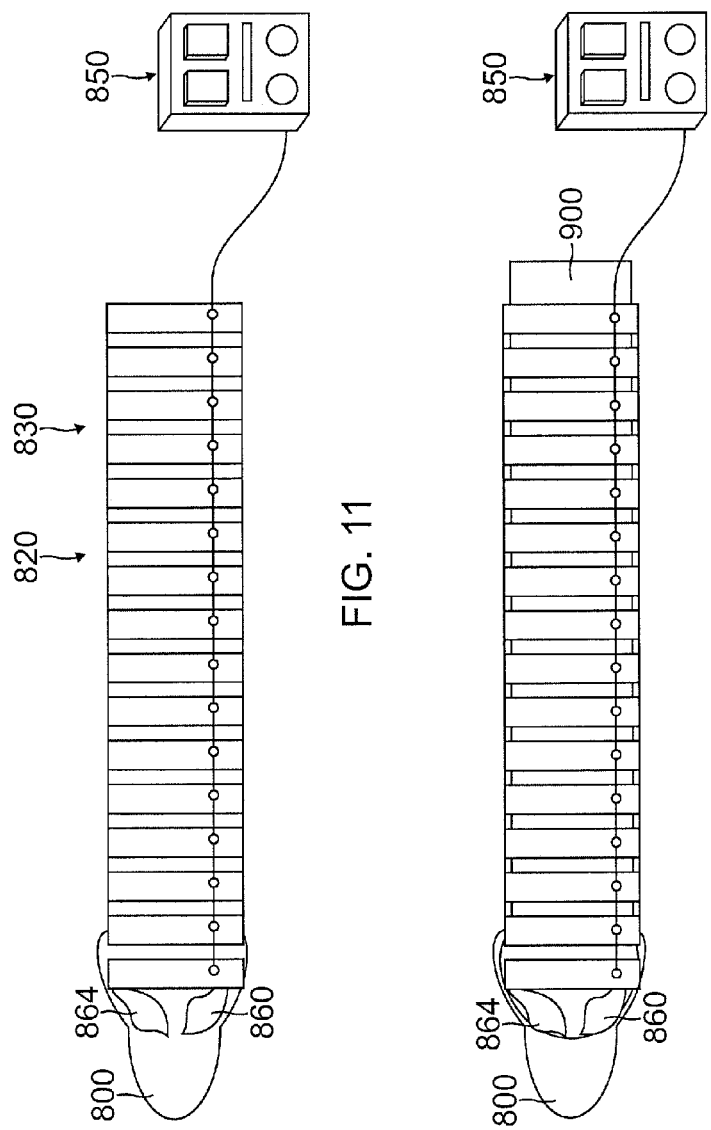

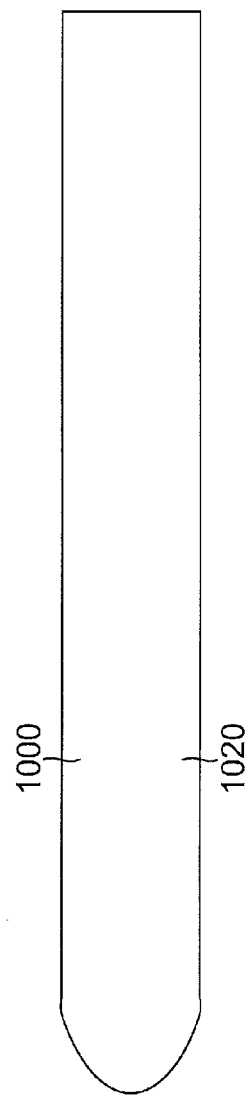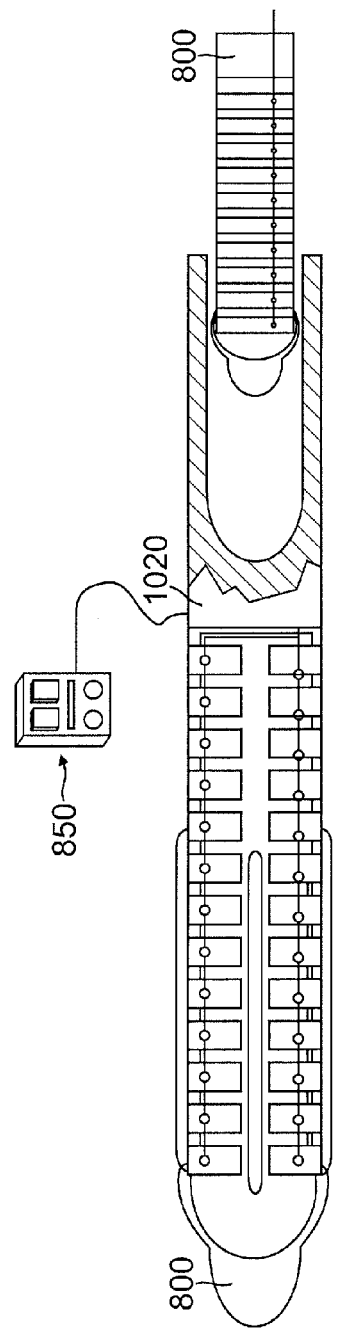

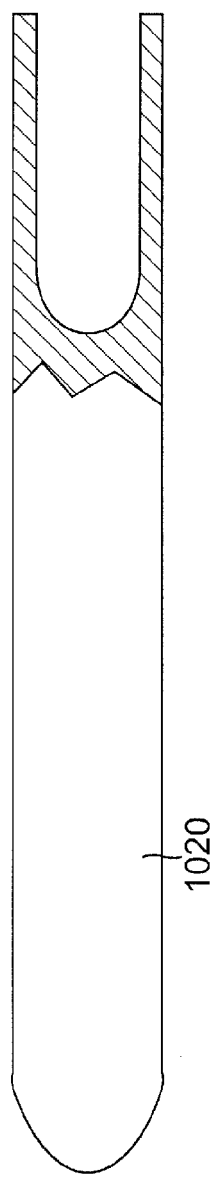
FIG. 19
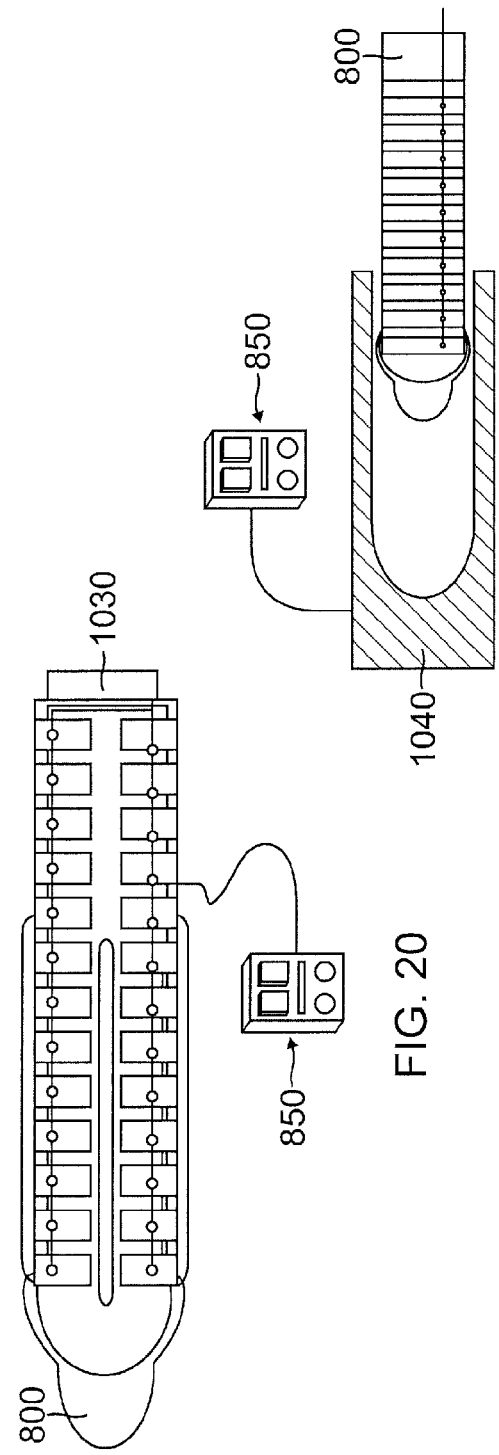
FIG. 20
FIG. 21

THERAPEUTIC PROSTHETIC DEVICE

CROSS-REFERENCE TO RELATED APPLICATIONS

This application is a continuation-in-part of U.S. application Ser. No. 11/938,661, filed Nov. 12, 2007, which is pending at filing of the present application, and which has been allowed and is scheduled to issue at U.S. Pat. No. 7,503,892 on Mar. 17, 2009, and which is incorporated by reference in its entirety herein.

This application is a continuation-in-part of U.S. application Ser. No. 11/733,347, filed Apr. 10, 2007, which is pending at filing of the present application, and which has been allowed, and which claims priority to U.S. Provisional No. 60/791,149, filed Apr. 10, 2006, both of which are incorporated by reference in their entireties herein.

BACKGROUND OF THE INVENTION

1. Field of the Invention

The therapeutic prosthetic device relates generally to the field of improving sexual relationships. More specifically, various embodiments of the therapeutic prosthetic device can be worn over a penis or inserted into a recipient's orifice to provide stimulation and sensation to both the wearer of the device and the recipient the device. The therapeutic prosthetic device addresses both male and female sexual and health issues. The prosthetic device uses sensors and tactile stimulators to convey sensations to or between the surface of the penis and to the vagina or other orifices or cavities. Devices and methods relating to embodiments of the invention enable men suffering from erectile dysfunction to feel a sensation of sexual intercourse or other stimulation on a flaccid, partially-erect, or erect penis. Devices and methods relating to embodiments of the prosthetic device help rehabilitate a woman's vagina. The prosthetic device enables women in experimenting and becoming much more open and conversant with midlife mental, physical and sexual sensations and changes in sexual response, allowing certain users to get the most out of "postmenopausal zest." The device can be used to improve sexual satisfaction and for therapeutic reasons in treating erectile dysfunction and other sexual or genitalia related conditions for both men and women.

2. Description of the Related Art

Both men and women can have sexual dysfunctions or changes in sexual response based on age, illness, medication or other factors that can make it difficult to perform sexually. The problems can be physical, emotional, or psychological, or a combination of such factors. Some solutions include drugs or other chemical or hormonal aid. However, the side effects of drugs are seldom completely understood, and may over the long term exacerbate the problem or lead to other problems. Other solutions include surgery to the sexual organs. Surgery is often inaccurate, risky, painful, and/or expensive, and may not address the real problem. Men have erectile dysfunction problems which render them unable to perform sexually. Women can have increased vaginal dryness. What is needed is a therapeutic prosthetic device that enables a person to experience the stimulation and sensations of a sexual event, while avoiding invasive and/or detrimental effects or drugs or surgery associated with other methods of addressing sexual dysfunction.

SUMMARY OF THE INVENTION

Accordingly, there is a need for apparatus, systems, and methods that safely and reliably produce sensations of a sexual event for one or both sexual partners irrespective of the condition of their sexual organs. This document discloses a system and method to simulate sexual copulation sensitivity, primarily for men and/or women who are unable to perform sexually for any reason.

In one embodiment, a system includes a therapeutic prosthetic device. The device includes a specially-designed, electronically-controlled stimulation prosthesis configured to fit over a flaccid, partially-erect, or fully erect penis. The prosthesis allows both partners in a sexual activity to feel the sensations of an actual sexual experience. The sensations are generated through the controlled release of electrical energy, which are controlled by a microprocessor and managed by one or more sensitivity sensors and direction-detection sensors included with the prosthetic device. In one embodiment, at least a portion of the exterior of the prosthesis includes an electronic user-controlled orifice stimulator. The user can be the man or the woman, or both. The user can control the exact and precise place to target stimulation, and the level or magnitude of stimulation administered.

The details of various embodiments are set forth in the accompanying drawings and the description below. Other features and advantages will be apparent from the description and drawings, and from the claims.

In one embodiment of the present invention, a therapeutic prosthetic device includes a prosthesis, a sensor, a microprocessor and stimulation material. The prosthesis has an outer surface and an inner cavity, where the inner cavity is sized and adapted to receive a penis. The sensor is integrated with the prosthesis for sensing a movement, pressure and/or force of the prosthesis in an activity. The sensor is configured to generate signals based upon such movement, pressure and/or force. The microprocessor receives signals from the sensor and is adapted to generate a signal intended to represent a sensation. The stimulation material covers at least a portion of the surface of the inner cavity for receiving the signal representing a sensation.

In another embodiment of the present invention, a therapeutic prosthetic device includes a prosthesis, a sensor, a microprocessor, a first stimulation material and a second stimulation material. The prosthesis has an outer surface and an inner cavity, where the inner cavity is sized and adapted to receive a penis. The sensor is integrated with the prosthesis for sensing a movement, pressure and/or force of the prosthesis in an activity. The sensor is configured to generate signals based upon such movement, pressure and/or force. The microprocessor receives signals from the sensor and is adapted to generate a signal intended to represent a sensation. The first stimulation material covers at least a portion of the surface of the inner cavity for receiving the signal representing a sensation. The second stimulation material covers at least portion of the outer surface of the prosthesis and is configured to receive the signal representing a sensation.

In another embodiment of the present invention, a prosthetic vaginal therapy device includes an elongate prosthetic body and a stimulation unit. The elongate prosthetic body includes an outer surface, the outer surface configured and shaped to resemble the look and feel of an erect penis. The stimulation unit includes a sensor, a microprocessor, and stimulation material. The sensor is integrated with the elongate prosthetic body for sensing a movement, pressure and/or force in an activity approximating sexual sensations. The sensor is configured to generate signals based upon such movement, pressure and/or force in an activity approximating sexual sensations. The microprocessor is configured for receiving signals from the sensor, with the microprocessor adapted to generate a signal intended to represent a sensation in an activity approximating sexual sensations. The stimulation material covers at least a portion of the outer surface for receiving the signal. In one embodiment the prosthetic vaginal therapy device also includes a controller configured to control the sensation. In one embodiment the unitary prosthetic body also includes an inner cavity configured to sense an insertion sensation of movement of an elongate body part in the inner cavity and generate an external sensation corresponding to the sensation movement of the elongate body part in the inner cavity. In one embodiment the elongate body part is a penis. In one embodiment the elongate body part is a finger. In one embodiment the prosthetic vaginal therapy device also includes a fluid delivery mechanism configured to deliver a fluid to the outer surface of the elongate prosthetic body for placement in a vagina. In one embodiment the fluid is selected from a group consisting of a lubricant, gel, liquid, hormone, medication, and sperm.

In another embodiment of the present invention, a method of therapeutic treatment of a vagina includes the steps of inserting an elongate prosthetic body in a vagina and simulating sexual sensation. The elongate prosthetic body includes an outer surface, a sensor, a microprocessor, and stimulation material. The sensor is integrated with the elongate prosthetic body for sensing a movement, pressure and/or force of the prosthesis in an activity approximating sexual sensations. The sensor is configured to generate signals based upon such movement, pressure and/or force in an activity approximating sexual sensations. The microprocessor is configured for receiving signals from the sensor. The microprocessor is adapted to generate a signal intended to represent a sensation in an activity approximating sexual sensations. The stimulation material covers at least a portion of the outer surface for receiving the signal. The simulating sexual sensation includes activating the stimulation material with the signal. In one embodiment the method of therapeutic treatment of a vagina also includes delivering a fluid from the elongate prosthetic body to the vagina. In one embodiment the fluid is selected from a group consisting of lubricant, gel, liquid, hormone, medication, and sperm.

In another embodiment of the present invention, a therapeutic prosthesis device for treatment of a sexual organ includes a therapeutic condom, a plurality of sensors, a microprocessor, and an external stimulation material. The therapeutic condom includes an outer surface and an inner surface, the inner cavity sized and adapted to receive an elongate body. The plurality of sensors is integrated with the therapeutic condom for sensing a movement, pressure and/or force of the unitary prosthetic body in an activity. The plurality of sensors is configured to generate signals based upon such movement, pressure and/or force. The microprocessor is configured for receiving signals from the plurality of sensors. The microprocessor is adapted to generate a signal intended to represent a sensation. The external stimulation material covers at least a portion of the outer surface of the therapeutic condom including a plurality of controllable stimulation elements in electrical communication with the microprocessor. In one embodiment the external stimulation material covering at least portion of the outer surface of the therapeutic condom is configured to receive the signal representing a sensation. In one embodiment the therapeutic prosthesis device also includes an internal stimulation material covering at least a portion of the inner surface for receiving the signal representing a sensation, the internal stimulation material comprising a plurality of controllable stimulation elements in electrical communication with the microprocessor. In one embodiment the therapeutic condom is configured to sense a sensation applied to the outer surface and simulate a similar sensation at a corresponding location on the inner surface. In one embodiment the therapeutic condom is configured to sense a sensation applied to the inner surface and simulate a similar sensation at a corresponding location on the outer surface. In one embodiment the stimulation material covering at least portion of the outer surface is configured to deliver electronically controlled stimuli based on electric signals generated from the microprocessor. In one embodiment the therapeutic condom is configured to expand or stretch as the penis may become fully erect during use of the device. In one embodiment the therapeutic prosthesis device also includes a fluid reservoir. In one embodiment the therapeutic prosthesis device also includes a fluid port configured for communication of at least one among the group consisting of fluid, lubricant, gel, liquid, hormone treatment, medication, and sperm to the outer surface. In one embodiment the therapeutic prosthesis device also includes a heating element. In one embodiment the internal stimulation material is controllable by one or more selected among the group consisting of the individual user, a partner, and a third party. In one embodiment the microprocessor is configured to receive instructions from one or more selected among the group consisting of a television, computer, movie, audio file, and Internet communication.

BRIEF DESCRIPTION OF THE DRAWINGS

These and other aspects will now be described in detail with reference to the following drawings.

FIG. 11 is a schematic side view of a stimulating condom embodiment of a therapeutic prosthetic device with a reservoir tip.

FIG. 12 is a schematic side view of the stimulating condom embodiment of FIG. 11 with a therapeutic prosthetic device with a reservoir tip on a penis.

FIG. 17 is a schematic side view of a one embodiment of a unitary therapeutic prosthetic device.

FIG. 18 is a schematic side view of the unitary therapeutic prosthetic device of FIG. 17 with embodiments of stimulation condoms.

FIG. 19 is a schematic partial cross-sectional side view of the unitary therapeutic prosthetic device of FIG. 17.

FIG. 20 is a schematic side view of a one embodiment of a stimulating condom configured for use by a recipient, such as an individual female, capable of remote communication.

FIG. 21 is a schematic side view of a one embodiment of a stimulating condom configured for use by an individual male, capable of remote communication.

Figure 1:
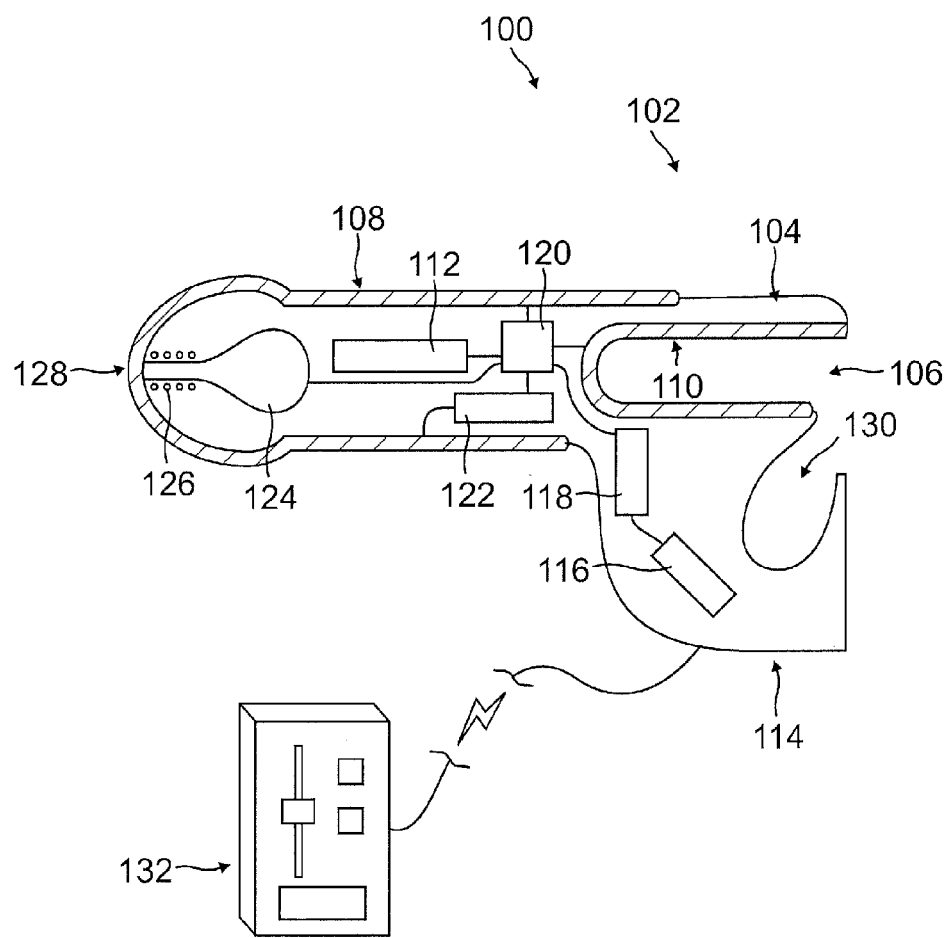
FIG. 1 is a schematic cross-section view of one embodiment of a therapeutic prosthetic device with an external controller.

Like reference symbols in the various drawings indicate like elements. Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF THE PREFERRED EMBODIMENT

This document describes a therapeutic prosthetic device, as well as systems and methods employing a therapeutic prosthetic device, for providing electronically simulated sensations and stimuli of a sexual experience, primarily for men and/or women who have sexual dysfunction problems. In various embodiments, the prosthesis can perform various functions.

For example, in various embodiments the prosthesis acts as a sexual therapy device for women. The device reduces reduce pain, bleeding, and uncomfortable feelings during sexual activity. The device can provide for a method for exercising or providing therapy to the genitalia. The device can provide for a method for exercising or providing therapy to the vagina. The device can be used to strengthen vaginal tissue and muscle. In one embodiment, controlled intermittent enlargement and shrinking of a portion of the device can provide a pleasured strengthening and exercise routine. In one embodiment, controlled inflation and deflation of a portion of the device can provide a pleasured strengthening and exercise routine. In one embodiment a controllable dilator can be used to stretch the vagina opening. In one embodiment the device can be used to relax tissue and muscle with gentle heat and massage. The device can provide sexual stimulation to women having been adversely affected by menopause and can help alleviate menopausal symptoms. The device allows lowered-libido women to introduce novelty into their relationships. The device can also aid in dealing with discomfort in a woman who is just getting back into a sexual relationship. The device can also be configured to provide for methods for women to precisely control delivery of stimulation to achieve greater levels of pleasure and orgasm.

In various embodiments the device can administer hormone treatments, drugs, fluids, particles, medications or other media. In one embodiment the device monitors the effectiveness of hormone treatments or medications on a regular basis, thereby reducing or avoiding a vicious destructive cycles of "try, try, and avoid" where patients with sexual dysfunctions quite therapy after a few attempts. In another embodiment the device operates as a functional in-vitro fertilization device, wherein the device can assist in artificial conception by providing sperm to the vagina, uterus, and/or fallopian tube inside the womb of a woman.

One embodiment of a therapeutic prosthetic device 100 in accordance with the present invention is illustrated at FIG. 1. The therapeutic prosthetic device 100 includes a prosthesis 102 configured and shaped to resemble the look and feel of an erect penis. The prosthesis 102 can be made of any rigid or semi-rigid yet soft material such as rubber, silicone, or the like. The prosthesis 102 includes an outer surface 104 and an inner cavity 106. The inner cavity 106 is sized and shaped to allow a flaccid, partially erect, or fully erect penis to be inserted therein. For example, the inner cavity 106 can have conductive pathways or channels built in to the structure to use gel or metal foil or other electrically or thermally conductive materials to direct sensations or stimuli to specific regions on the surface of the penis. In one embodiment the surface of the inner cavity 106 includes a flexible, stretching mesh or fabric like a sock configured to hold a flaccid penis. The mesh is configured to expand or stretch as the penis may become fully erect during use of the device. The man can wear a condom to collect any fluid or semen while using the device. In some embodiments (described below) a specially designed condom can be specially configured with conductive media or sensors to communicate with the inner cavity 106 of the therapeutic prosthetic device 100. The specially designed condom can be disposable. In one embodiment a specially designed condom contains fluids to provide a much greater stimulation experience due to the design and coating on the condom.

In various embodiments the therapeutic prosthetic device 100 includes external stimulation material 108 that covers at least a portion of the outer surface 104, an internal stimulation material 110 that covers at least a portion of the inner cavity 106, or both. In some preferred embodiments, the external stimulation material 108 covers a major portion of the outer surface 104, and the internal stimulation material 110 covers a major portion of the inner cavity 106. The external and internal stimulation material 108, 110 are electronically controlled. In one embodiment the external and internal stimulation materials 108, 110 are configured to receive and/or deliver electronically controlled stimuli based on electric signals generated from a microprocessor 120, discussed further below.

In one embodiment the external and internal stimulation materials 108, 110 are configured to receive and/or deliver electronically controlled stimuli based on electric signals generated from a sensitivity and/or direction sensor 112. In certain embodiments the sensor 112 can be mounted on the outer surface 104, or contained within the prosthesis 102, or be configured to be both mounted on and contained within the prosthesis 102. The sensor 112 can be electrically or physically connected with the external stimulation material 108 and/or internal stimulation material 110 through one or more processors or controllers. In various embodiments the sensor 112 or sensors described herein can be any of a variety of sensors known in the art that can be used to measure physical characteristics, length, depth, girth, engorgement, pressure, temperature, pH, salinity, viscosity, moisture, humidity, or other characteristics through the use of any sensors in the art. For example, one or more light or IR or ultrasound emitter/detector pairs, pressure pads, piezoelectric sensors, fluid bladders, thermometers, etc. can be used. Other sensors may include a transducer, temperature sensor, thermometer, thermocouple, thermistor, thermostat, bolometer, ohmmeter, multimeter, galvanometer, ammeter, voltmeter, hall effect device, pressure sensor, barometer, barograph, pressure gauge, flow sensor, anemometer, flow meter, mass flow sensor, acceleration sensor, accelerometer, position sensor, selsyn, strain gauge, oxygen sensor, pH electrode, optical sensor, fiber optic sensor, ultrasonic sensor, microphone, MEMS sensor, or other sensors known in the art.

In one embodiment the therapeutic prosthetic device 100 is configured to directly map and simulate the sensation applied to the outer surface 104 of the prosthesis 102 and apply a similar sensation to the penis inside the inner cavity 106 and surrounded by the internal stimulation material 110. For example, the sensor 112 measures the depth to which the prosthesis 102 is inserted into a cavity, such as a vagina. The sensor 112 can be any type of pressure sensor, or a sensor strip that generates an analog or digital signal based on the pressure applied to one or more regions on or around the prosthesis 102. The sensor 112 can provide a precise correlation or simulation of stimulation on the penis with the internal stimulation material 110. As the depth to which the prosthesis 102 is inserted into a cavity, stimulation to the penis encased in the inner cavity 106 and surrounded by the internal stimulation material 110 can be configured to map a sensation of electric or vibration or pressure that begins at the tip of the penis and moves proximally down the penis toward the man's body, the deeper the outer surface 104 of the prosthesis 102 is inserted. As the outer surface 104 of the prosthesis 102 is retracted out of a body cavity, the internal stimulation material 110 moves distally down the penis shaft toward the penis tip. When the outer surface 104 of the prosthesis 102 is fully removed from the body cavity, stimulation to penis can cease. With the example provided, in order to precisely match the sensation mapped from the outer surface 104 of the therapeutic prosthetic device 100 to the inner surface 106 the sensor and the internal stimulation material 110 will need to be calibrated. To the extent that a flaccid penis is inserted into the internal stimulation material 110, a separate or combination sensor located in the inner surface 106 can gauge the extent and location of the tip of penis to correlate to the sensation at the tip of the prosthesis 102. In one embodiment the mesh material inside inner surface 106 will stretch along with the penis as it may vary in length due to varying stages of erection. The internal stimulation material 110 can be configured to be attached to the same mesh material to move along with the penis through varying stages of erection. Alternatively, a sensor in the inner surface 106 can determine the location based on a sensor which can measure pressure, temperature, or light reflection or emission or other characteristics to determine the location of the penis within the inner surface 106.

Figure 4:
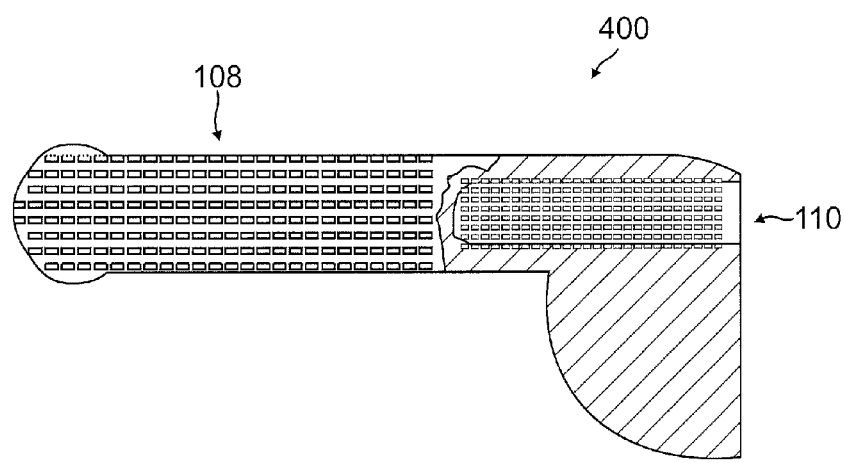
FIG. 4 is a schematic partial cross-section view of an embodiment of a therapeutic prosthetic device with a grid material.
Figure 5:
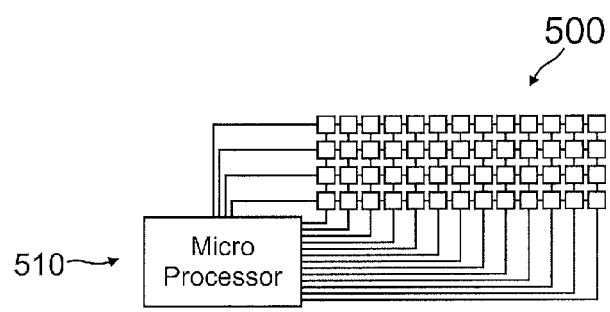
FIG. 5 is a schematic side view of an embodiment of a microprocessor connected to a grid material on a therapeutic prosthetic device.

In one embodiment, as discussed further below with respect to FIGS. 4 and 5, the external and internal stimulation materials 108, 110 are covered with a grid or matrix of sensors and/or stimulators. The sensors and/or stimulators can be configured to map the surface of the penis or the exterior surface of the prosthesis 102 in order to correlate sensations from one location to another. In other embodiments, the grid of stimulators can use preprogrammed stimulation patterns as communicated from a controller or microprocessor, through the device and/or through an external computer or wireless communication system. More discussion of the sensors and stimulators is provided below.

In one embodiment, the stimulator or exciter material is a transcutaneous electrical nerve stimulation (TENS) pad material having one or more electrodes to administer an electrical current at a particular frequency. Alternatively, the stimulator can deliver vibration energy, such as through one or more piezoelectric wafers. The stimulator material can include one or more discrete stimulation areas. In various embodiments, a single uniform stimulator may be used, a plurality of stimulators may be arranged in rings, stripes, a grid, or a combination of arrangements can be used. In various embodiments, the stimulator or external stimulation materials 108 electrically stimulates tissue such as muscle or other surface or subsurface tissue within the orifice or cavity, thereby generating physiological responses such as quivering or pulsating, and accentuating physiological conditions such as subsurface abnormalities. Thus, abnormalities can be brought to the surface inside of an orifice or cavity. In some embodiments quivering can also make the wall of the vagina more porous, and more effective at absorbing fluids.

In various embodiments various components of the device can be housed or located in a shaft within the prosthesis 102 and/or in a bag 114 which may correspond to a scrotum. Various component of the device may include one or more batteries 116, controllers 118, microprocessors 120, fluid reservoirs 122 and 124, heating elements 126, and ports in communication with the outside of the device 128.

In various embodiments, the controller 118 is wired to one or both stimulation materials 108 and 110 and can communicate electric signals through an analog or digital circuit establishing certain electrical stimulation patterns based on one or more signals to the sensor 112. In one embodiment one or more of the stimulation materials 108 and 110 can act both as a stimulation material as well as a sensor, communicating signals based on pressure, contact, heat, or other physical characteristics to a controller 118 of 132 and/or to the microprocessor 120. The microprocessor 120 can be embodied in one or more processors. The sensor 112 provides input to the microprocessor 120 as to the movement (directionally, degree of force or sensitivity, etc.) and pressure experienced by the prosthesis 102 for approximating sexual sensations. The microprocessor 120 then generates an electronic representation of the sensation and delivers the electronic representation to the internal stimulation material 110, for providing sexual sensations to the penis, and/or to the external stimulation material 108 for providing sexual sensations to a vagina or other cavity. In various embodiments, the stimulation intensity and focus of stimulation is controlled by an individual user or by a partner, or third party. Control software can be downloaded or updated on a regular basis. In certain embodiments, the controller 118 and/or microprocessor 120 can receive instructions from a TV, computer, movies, audio, etc. and the device can be pre-programmed for specific conditions, monitoring of usage and results, and can be controlled for therapeutic group sessions.

The controllers 118 control and modulate the microprocessor 120 so as to adjust the level and intensity of the electronic representation of the simulated sensations. The therapeutic prosthetic device 100 can be controlled by any means possible from wireless hand-held transmitters, wired controllers, computers, cell phones, air waves, embedded signals in movies, songs, or internet or software programs. In one embodiment a mind-device interface is contemplated whereby functions of the therapeutic prosthetic device 100 might be controlled by the mind or through interfaces that help direct thoughts into actions. For example, devices for actuating artificial limbs for use with amputees, paraplegics, quadriplegics, partial or complete paralysis or other conditions. Brain mapping techniques can be converted for use to drive the prosthesis. These could be accomplished by direct or indirect wiring or monitoring of feedback and signals from the brain or nerves of a user so as to provide functionality to disabled individuals wishing to experience sex and/or please their partner. The controller 118 can direct all aspects of the therapeutic prosthetic device 100 from pumps, limiters, illumination, stimulation, transmissions, etc. A battery supply can also be provided within the controller 118 to drive the controller 118, and/or other components such as a processor or the entire device 100. An optional external controller 132 provides independent control of the electronic stimulation level to the penis and/or cavity, and onto the prosthesis 102 to give users full control over the intensity of the stimulation and sensations. The external controller 132 can communicate to the microprocessor 120 via a wired or wireless communication channel.

The fluid reservoirs 122 and 124 can contain lubricant, drugs, hormones, semen, or any type of fluid to be delivered to a bodily cavity, such as the vagina. For example, in one embodiment fluid reservoir 124 is a fluid bladder containing a fluid which can be heated with heating element 126 to deliver the fluid at, near, or above body temperatures through a port 128 to the vagina. The fluid can be configured to simulate semen being ejaculated from the reservoir by control 118 or 132, and can be configured to correspond to actual ejaculation or orgasm in one or both of the sexual partners. In another embodiment, the fluid can be viable semen for insemination or impregnation purposes. In one embodiment, the fluid reservoirs 112 and/or 124 can be used to collect fluids or samples or take measurements of temperature, pH or other characteristics from the body cavity, such as a vagina.

In one embodiment of the therapeutic prosthetic device 100 a scrotum chamber 130 is provided in the bag 114 to house the male's scrotum and can be configured to cup the scrotum in such a manner to hold the device to the male's body by cupping on to the scrotum to hold the device in place. In another embodiment (not illustrated) the therapeutic prosthetic device 100 can also include a strap to attach to or around the buttocks or around one or more thighs to hold the device in place. In another embodiment the therapeutic prosthetic device 100 can be attached to the skin with a non-permanent adhesive, or can be attached to clothing such as underwear with buttons, Velcro, or the like. Any of these approaches, or any combination of approaches may be used to secure the therapeutic prosthetic device 100 to the man. Furthermore, one or more external controllers 132 can be in electrical communication by wired or wireless connection to control one or more of the stimulation materials 108 and 110. The external controllers 132 can be hand held devices used by the sexual partners or may be connected to a third party, or to a computer or other communication device.

In operation, as the therapeutic prosthetic device 100 is placed over a penis which is inserted in the inner cavity 106. The scrotum can optionally be placed in scrotum chamber 130. As described below, a bladder may be inflated to secure the penis. In another embodiment, suction can be used with a pump or tube fluidly connected to the inner chamber 106 to secure the device to the penis. The device 100 is inserted into a cavity such as a vagina. The penis inside the inner cavity 106 receives electronically generated sensory signals, preferably directed to the tip of the penis head, via a portion of the internal stimulation material 108. As the therapeutic prosthetic device 100 is inserted further into the cavity, the electronically generated sensory signals are delivered further along the penis shaft by the internal stimulation material 108.

Figure 2:
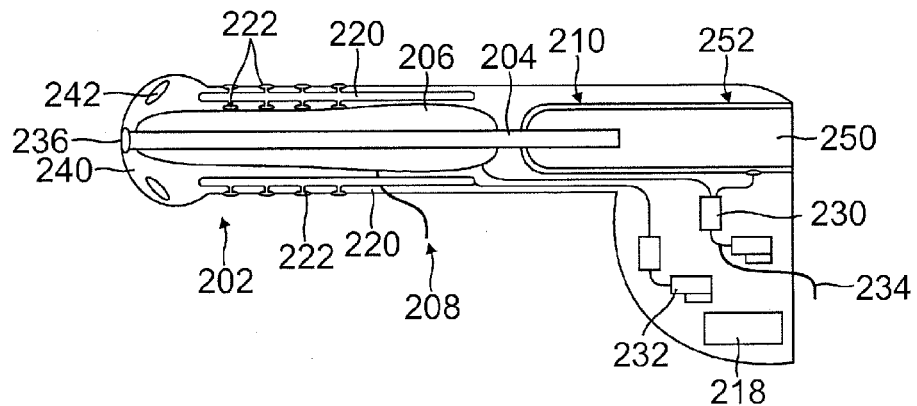
FIG. 2 is a schematic cross-section view of an embodiment of a therapeutic prosthetic device.

In another embodiment of a therapeutic prosthetic device 200, illustrated at FIG. 2, the same or similar features and functions of the therapeutic prosthetic device 100 described above can be used in conjunction or substituted in a number of ways. For example, prosthesis 202 is similar to prosthesis 102 described above, but can be detachable as shown in FIG. 3. The various prostheses 102, 202, etc. can have outer surfaces 104 with varying sensors and features that can be swapped out depending on the therapeutic or sexual application. Various surface textures, colors, hardness, durometers, and sensors configurations can be combined with different detachable prostheses 202. As discussed above, various sensors can be used. In one embodiment the therapeutic prosthetic device 200 includes one or more sensor strips 204 which can sense and communicate sensation from the prosthesis 202. The strip(s) 204 can be configured to be oriented longitudinally, laterally, circumferentially, or otherwise. The therapeutic prosthetic device 200 can have similar controllers 218 as the therapeutic prosthetic device 100 controller 118 and other similar components.

In one embodiment the prosthesis 202 includes one or more prosthesis bladders 206 that adjusts the diameter (or girth) of the prosthesis 202. This prosthesis bladder 206 can be manually or digitally controlled and is useful for women whose vagina tissue have become tight, brittle and constricted due to lack of sex or manual stimulation, and/or a woman who prefer experimenting with different size penis. Size can be increased simply by filling the bladder with air, gas, liquid, gel, etc, with a tube 208 to a manual bulb with a valve, or it can be controlled by electronic pumps inside or outside the device and controlled by a processor or control. In use, the girth of the prosthesis 202 can be inserted while in a fairly limp (non-rigid) configuration by removing some inflation air, liquid, gel, gas, etc., and allow the users to control the hardening of prosthesis 202, replicating real life penis function. Users can have direct control over how large, how hard, how long, how big in size the prosthesis will be through the use of one or more expansion bladders 206. This is to allow users to replicate various sexual experiences with the device 200. Inflation and deflation of the prosthesis bladder 206 can be digitally controlled to simulate a pulsating penis at various stages of excitement and nearing and experiencing orgasm. Control of the size of the prosthesis 202 reduces the chance of discomfort in a woman just getting back into a sexual relationship, especially menopausal women. It can also be used to strengthen vagina tissue and muscle. Controlled inflation and deflation of the prosthesis bladder 206 can provide a pleasured strengthening and exercise routine. It can be used as a controlled dilator to stretch the vagina opening, or to relax tissue and muscle with gentle heat and massage.

One embodiment the therapeutic prosthetic device 200 includes one or more inner cavity bladders 210. The inner cavity bladder 210 can operate in similar ways as the prosthesis bladder 206, but is directed to sensations delivered to the penis in the inner cavity. Once the penis is in place in the inner cavity, the inner cavity bladders 210 can be inflated to secure the penis firmly in place. The inner cavity bladders 210 provide a much closer proximity to stimulators and controls how the penis will be stimulated. Inflation and deflation of an inner cavity bladder 210 can be digitally controlled to simulate a pulsating vagina to the surface of the penis, including various stages of excitement and nearing and experiencing organism. In one embodiment sensors, such as pressure sensors, are attached to the prosthesis bladder 206 and the inner cavity bladder 210 to map changes in pressure between the inner cavity and outer surface of the prosthesis.

One embodiment the therapeutic prosthetic device 200 includes one or more fluid bladders 220. These fluid bladders 220 can serve numerous purposes for health and stimulation purposes. The fluid bladders 220 can be comprised of one or a few larger chambers, or a network of smaller chambers to house various fluid media. The chambers in the fluid bladders 220 can be segmented into smaller cells to contain different media and/or to provide structural strength to the prosthetic device 200. Bladders may contain separate contents or mix together into one substance. For example, in various embodiments, the fluid bladder 220 may be associated with or in communication with the prosthesis bladders 206 and/or the inner cavity bladders 210. The fluid bladders 220 can provide for the controlled discharge of lubrication and other stimulation gels, liquids, etc. to the inner chamber or the outer surface of the device 200. The fluid bladders 220 can provide for controlled discharge of medical creams, gels, tissue conditioners, pain relievers, etc., (Vagifem, Estradiol cream, Estrogen, testosterone, hormone replacement), and/or deliver lubricants that coat vagina tissue walls to stimulate, condition, repair damaged tissue, creams to off-set the spread of sexually transmitted diseases (STD's), liquids, gels, etc, to warm (and/or chill) vagina, tissue, or simply to provide sufficient lubrication to simulate the thick and gliding mucus that flows during sexual arousal to help repairs vaginal dryness.

Associated with the fluid bladders 220 are one or more fluid channels and fluid ports 222. In one embodiment one or more ports 222 allow for communication of fluids, lubricants, gels, liquids, etc, contained in the bladders can be discharged into the body. In one embodiment the device can administer hormone treatments, medications and monitor the effectiveness of hormone treatments or medications on a regular basis, thereby reducing or avoiding a vicious destructive cycles of "try, try, and avoid" where patients with sexual dysfunctions quite therapy after a few attempts. In another embodiment the device operates as a functional in-vitro fertilization device, wherein the device can assist in artificial conception by providing sperm to the fallopian tube inside the womb of a woman. In another embodiment one or more ports 222 allow for communication of fluids, lubricants, gels, liquids, etc, contained in the body cavity or penis to be collected and stored in the device 200. In one embodiment one or more ports 222 have a valve or controllable opening to time the opening of the channels to the interior or exterior of the therapeutic prosthetic device 200.

One embodiment the therapeutic prosthetic device 200 includes one or more digitally controlled inflators 230 that control the inflation of gases, liquids, air, etc. in the various bladders and monitors and directs pressure to ensure proper inflation or deflation of bladders without any risk to users. The digitally controlled inflators 230 direct fluid media from one or more inflation pumps 232 and/or manual inflation tubes 234 and distribute pressure or fluid where the user or controller selects. The inflation pump 232 provides air, liquid, gas, etc. to inflate or deflate various bladders for controlling size, grip, and sensation in the bladders as well as for discharging or collecting fluid and other samples. The manual inflation tube 234 can be similar to the tube 208 described above, and can inflate bladders and provide pressure to discharge fluid bladders by mouth and/or external pump, bulb, etc. Various fluid pumps 232 can be dedicated to specific tasks, such as a fluid pump specifically dedicated to discharging fluids. In one embodiment, a fluid port 222 may be specially configured to act as a discharge port 236 which can discharge simulated ejaculation fluid or to release actual ejaculates containing sperm, and/or any other body fluid. Thus, the therapeutic prosthetic device 200 can also be used as a functional in-vitro fertilization device to help with assisted conception by providing sperm to the fallopian tube inside the womb of a woman.

In certain embodiments the therapeutic prosthetic device 200 can further be provided with additional functionality for medical monitoring and therapeutic purposes directed to a body cavity, such as a vagina. For example, with respect to the assisted conception embodiment described above, the discharge port 236 can be directed to the cervix with a camera or other imaging device in communication with an external monitor. An imaging device 240 may optionally be included at the distal end of the prosthesis 202 so users can monitor activities within the body cavity while the therapeutic prosthetic device 200 is inserted. Associated with the imaging device 240 may be illumination devices such as LED's, controllers, lenses, etc. to communicate the internal condition, reaction, movement, etc. of portions of the body cavity with a wired or wireless connection to a monitor, TV, computer, printer, or any viewing or data capture or transmission device. In another embodiment, other sensors such as a thermometer 242 can be used to monitor interior vagina tissue and muscle for indications of illness, infection or other conditions.

In one embodiment the inner cavity 250 of the therapeutic prosthetic device 200 is lined with one or more warming elements 252. The warming elements 252 can provide greater comfort or stimulation to the penis. In various non-illustrated embodiments, warming elements 252 can be used on or near the surface of the prosthesis 202 for comfort or stimulation of the body cavity, or the warming elements 252 can be used to heat fluids in various bladders for warmed media, such as lubrication or ejaculate matter.

Figure 3:
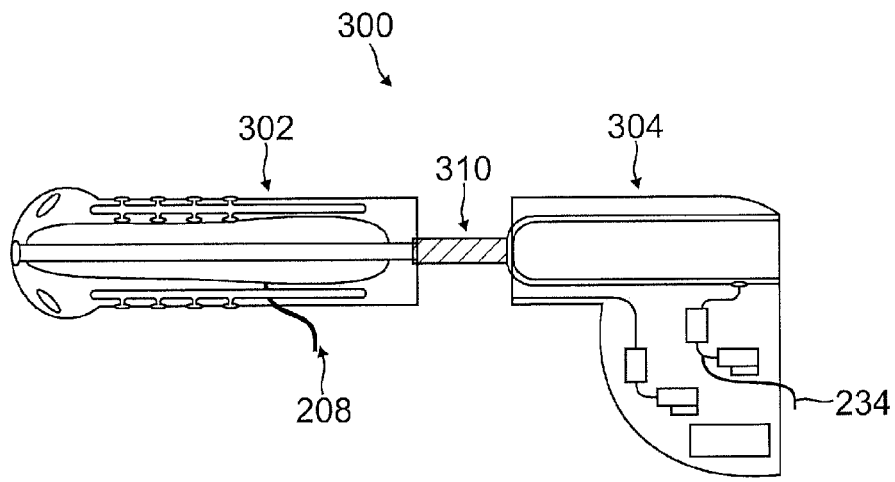
FIG. 3 is a schematic partially exploded cross-section view of an embodiment of a therapeutic prosthetic device with a detachable prosthetic shaft.

In one embodiment, a therapeutic prosthetic device 300 comprises a penile extension 302 and a penis stimulation module 304. The penile extension 302, like the detachable prosthesis 202 described above, can be used for body cavity stimulation and/or masturbation or therapeutic purposes. The penis stimulation module 304 is directed to stimulating the male user and is specifically designed to hold a penis in any state of arousal and to provide stimulation at an intensity controlled by the user. FIG. 3 illustrates a partially disassembled therapeutic prosthetic device 300 with an attachment mechanism 310 for mechanically, fluidly, optically and/or electronically connecting a penile extension 302 and a penis stimulation module 304. The mechanical connection of the attachment mechanism 310 can interlock both primary components of the therapeutic prosthetic device 300. In some embodiments this may entail a bolt, screw, clamp, clasp, snap fit, thread, or locking interface. The attachment mechanism 310 provides connection for electronic, digital, video, imaging, fluid, and/or air as well by connecting fluid, optic, and/or electrical lines. In one embodiment the therapeutic prosthetic device 300 can be supplied as a complete single unit or in pieces that can be connected or interconnected with each other. Different components, sensor, sizes and functionality vary depending on the connections made.

In one embodiment, as discussed above with respect to FIGS. 4 and 5, a matrix or grid of sensors can be used to sense motion, position and condition in the inner chamber 106 and/or the outer surface 104. In one embodiment, a grid or matrix of sensors can be configured to map the surface of the penis or the exterior surface of the prosthesis 102 in order to correlate sensations from one location to another. In one embodiment the external and/or internal stimulation materials 108, 110 comprise a grid or matrix of stimulators to convey the sensation from one set of mapped sensations detected from the sensors of one region of the inner chamber 106 or the outer surface 104 to the stimulators of the other respective region of the corresponding outer surface 104 or inner chamber 106. In one embodiment, the stimulators are TENS pads that are properly electrically connected to a grid of wires or conductive channels in a set of flexible layers in electrical communication with a control and/or microprocessor. The grid elements 500 can be arranged in a pixel-style arrangement to be in electric communication with signals to or from a microprocessor 510 as shown in FIG. 5. Whether the grid elements 500 are sensors or stimulation materials, the drivers and control mechanisms for electric communication between a grid and microprocessor are known in the art. The size of the grid elements 500 can vary from one to thousands of "pixel" elements, such as 1 element, or 2, 4, 8, 16, 32, 64, 128, 256, 512, 1024, or other configurations depending on the desired resolution and space available. Through the use of MEMS or nanotechnology there is no discernable limit to the number of grid elements that can be used. Enough grid elements should be put in place to sufficiently map or convey stimulation (electrical, vibrational, mechanical, or otherwise) to the respective body tissue.

In other embodiments, the grid of stimulators can use pre-programmed stimulation patterns as communicated from a controller or microprocessor, through the device and/or through an external computer or wireless communication system. For example, the user can use a hand held controller to activate certain patterns at any time. Or, specific stimulation patterns or random stimulation patterns can result from sensed or timed events. Stimulation running up and down the prosthesis or penis can vary, from circumferential patterns, to longitudinal patterns, twirling patterns, swirling patterns, etc. Specific stimulation patterns or focus points can be provided to prevent premature ejaculation as well. Certain stimulation patterns can be provided to delay ejaculation if the user chooses to do so.

Figure 6:
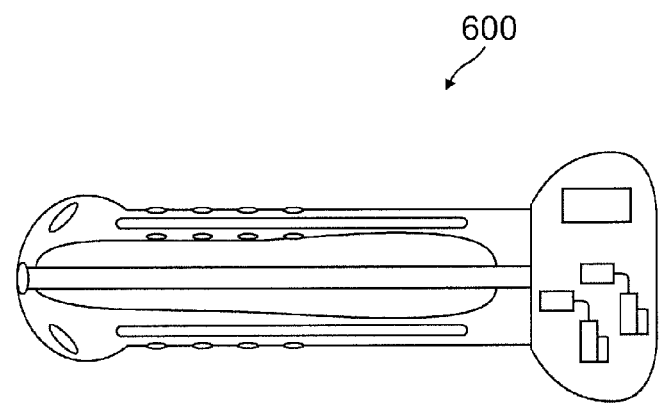
FIG. 6 is a schematic cross-section view of an embodiment of a therapeutic prosthetic device configured for use by a recipient, such as an individual female.
Figure 7:
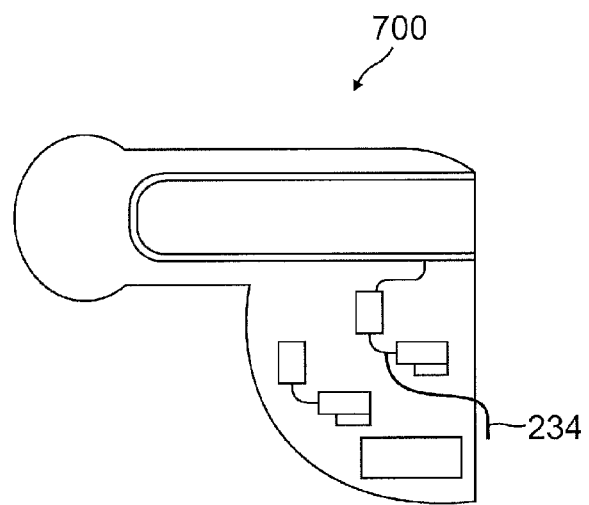
FIG. 7 is a schematic cross-section view of an embodiment of a therapeutic prosthetic device configured for use by an individual male.

In one embodiment the stimulators follow patterns communicated remotely from one therapeutic prosthetic device to another, in the same room, different room, different state, country, or otherwise. Communication of stimulation patterns can be provided wirelessly, through the Internet, or otherwise. For example, separate individual components can be used for separate devices, as is shown in the embodiments in FIGS. 6 and 7. In one embodiment, a therapeutic prosthetic device 600 configured for use by an individual female includes many of the features described with respect to the therapeutic prosthetic devices herein, but does not include an inner chamber for penis insertion. In one embodiment, a therapeutic prosthetic device 700 configured for use by an individual male includes many of the features described with respect to the therapeutic prosthetic devices herein, but does not include sensors or ports, or other components for the outer surface of the device.

In some embodiments, a therapeutic prosthetic device can be configured like a condom, such as a therapeutic condom. In one embodiment a prosthetic body corresponds to a therapeutic condom. In various embodiments, therapeutic condoms can reduce the need for a larger scale electro-stimulation equipped prosthetic device. For example, when male is able to achieve and maintain an erect or semi erect penis 900 by wearing a therapeutic condom, use of rigid or semi-rigid structures to simulate an erect penis may not be necessary. In various embodiments, a therapeutic condoms is provided with stimulation material surrounding the inside and/or outside of the condom, designed to provide sexual stimulation for the user(s) of the therapeutic device, female, male and/or both. Stimulation can be directed to the outside of the condom (stimulating the recipient's orifice), inside the condom with direct contact to the penis (stimulation to wearer), or on both sides to stimulate both partners at the same time. In one embodiment the therapeutic condom is wrapped in a foil similar to currently marketed condom packaging. In various embodiments the electronic stimulation material is integrated into the condom, along with fluid reservoirs that can contain lubricant, drugs, hormones, or other media. In one embodiment a therapeutic condom is expandable in length and girth and other dimensions to accommodate any size penis. In one embodiment a therapeutic condom used for a flaccid or un-erect penis will be more rigid (with a higher durometer or more rigid structure) so as to extend to keep the penis more firm. This can lead to more area to stimulate and result in higher pleasure. In one embodiment stimulation material can be used in conjunction with dispensing medication, wherein the tissue absorption of the medication is improved or more effective in conjunction with the stimulation than it would be simply applied to the tissue surface.

Figure 8:
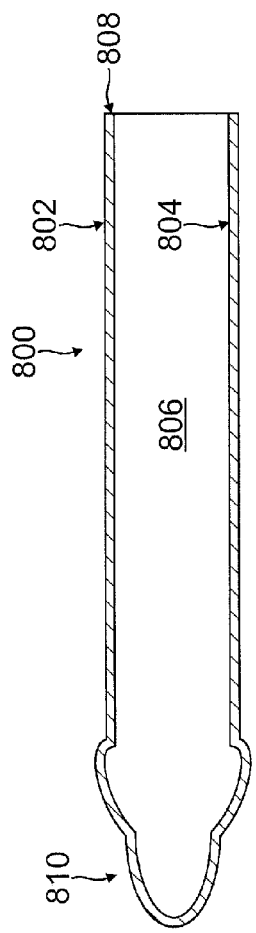
FIG. 8 is a schematic cross-sectional side view of a condom embodiment of a therapeutic prosthetic device.

FIG. 8 illustrates one embodiment of a therapeutic condom prosthetic device. In one embodiment a therapeutic prosthetic device is a therapeutic condom 800. Therapeutic condom 800 can have any combination of one or more of the characteristics or features of any of the embodiments of the various therapeutic prosthetic devices disclosed herein. The therapeutic condom 800 comprises an outer surface 802, an inner surface 804 defining a cavity 806 that is configured to be filled with a flaccid, partially erect, or fully erect penis. The inner surface 804 transitions to the outer surface 802 at opening 808. The therapeutic condom 800 also comprises a distal end 810. In one embodiment the distal end 810 is closed. In various embodiments the distal end 810 can be shaped to conform to various shapes. In one embodiment a distal end 810 is configured in the form of a penis. In one distal end 810 embodiment, such as a penis shaped tip, is effective in providing a piston-like action to force sperm up into the uterus.

In various embodiments, the therapeutic condom can be formed and manufactured in a manner similar to a condom. In various embodiments the therapeutic condom 800 is made of a base material same or similar to other condoms, such as latex, polyurethane, or other natural or synthetic materials. In various embodiments the therapeutic condom 800 can be waterproof, textured, or include a medication or lubricant.

In one embodiment the therapeutic condom 800 includes stimulation material 820. The stimulation material 820 can be any type of stimulation material disclose herein, including any grid element 500. In various embodiments the stimulation material 820 can stimulate with temperature (heating or cooling), vibration, frequencies, electrical current, or other sensory forms. In various embodiments the stimulation material 820 can be any form of electrical stimulation. In one embodiment the stimulation material 820 uses Transcutaneous Electrical Nerve Stimulation (TENS).

In one embodiment the stimulation material 820 is an external stimulation material 822 that covers at least a portion of the outer surface 802. In one embodiment the stimulation material 820 is an internal stimulation material 824 that covers at least a portion of the inner surface 804. In one embodiment the stimulation material 820 is an external stimulation material 822 and an internal stimulation material 824. In one embodiment the external stimulation material 822 and an internal stimulation material 824 are in direct electrical communication with each other. In one embodiment the external stimulation material 822 and an internal stimulation material 824 are in controlled electrical communication with each other through circuitry. In one embodiment the external stimulation material 822 and an internal stimulation material 824 are in controlled electrical communication with each other through a processor. In one embodiment the external stimulation material 822 and an internal stimulation material 824 are the same unitary bodies. In one embodiment the external stimulation material 822 and an internal stimulation material 824 stimulate both the inside and outside of the therapeutic condom simultaneously. In some embodiments, the external stimulation material 822 covers a major portion of the outer surface 802, and the internal stimulation material 824 covers a major portion of the inner surface 804. In one embodiment the external and internal stimulation material 822, 824 are electronically controlled. In one embodiment the external and internal stimulation materials 822, 824 are configured to receive and/or deliver electronically controlled stimuli based on electric signals generated from a controller 850. In one embodiment stimulation material 820 is flexible. In one embodiment stimulation material 820 is roughly the thickness of one sheet of paper. In one embodiment stimulation material 820 is roughly the thickness of two sheets of paper. In various embodiments, the stimulation material 820 can be less than 5 mm thick, less than 1 mm thick, less than 0.1 mm thick, or less than 0.05 mm thick.

In various embodiments, the therapeutic condom can include structure, features, characteristics and capabilities of any of the therapeutic prosthetic devices, including but not limited to 100, 200, 300, 400, 500, 600, and 700, discussed herein. For example, the therapeutic condom 800 can have one or more sensors 830 similar to any type of embodiment of sensor 112 or grid elements 500 described above. In one embodiment sensor 830 measures electric potential. In one embodiment sensor 830 is inductive. In various embodiments sensor 830 measures pressure, speed, orientation, temperature, salinity, coefficient of friction, or other characteristics. In one embodiment, sensor 830 has a similar structure as stimulator 820. In one embodiment, sensor 830 measures blood pressure and/or blood flow. In one embodiment sensor 830 measures blood pressure and/or blood flow as a safety measure to avoid over-stimulation by reducing or stopping stimulation in response to certain sensor readings. In one embodiment a stimulation regulator (not illustrated) reduces or prevents the likelihood of over stimulation and/or injury by users of the device by reducing, modulating, altering, or stopping stimulation signals to the device in response to a signal or sensor 830 reading indicating that the stimulator needs regulation. In one embodiment the stimulation regulator is a circuit. In one embodiment the stimulation regulator is an internal circuit. In one embodiment the stimulation regulator is in a controller 850.

In one embodiment the therapeutic condom 800 is configured to directly map and simulate the sensation applied to the outer surface 802 and apply a similar sensation to the penis inside the inner surface 804 and at least partially in contact with internal stimulation material 824 in a manner same or similar to the embodiment of the therapeutic prosthetic device 100 described above with respect to its outer surface 104 of the prosthesis 102 and apply a similar sensation to the penis inside the inner cavity 106 and surrounded by the internal stimulation material 110. In some embodiments, stimulation material 820 may be used on the inside, outside, both sides, or neither side of the therapeutic condom 800. In some embodiments, sensor 830 may be used on the inside, outside, both sides, or neither side of the therapeutic condom 800. In one embodiment a sensor 830 is configured to determine the depth of penetration of a penis in an orifice, such as a vagina.

In various embodiments sensors 830 and/or stimulation material 820 are in electrical communication with each other or a controller 850 with connectors 840. In one embodiment the connector 840 is a wire. In one embodiment connector 840 is a conductive strip. In one embodiment connector 840 is a wireless communication. In various embodiments the external and internal stimulation material 822, 824 and/or sensors 830 can comprise single electrodes or electrical surfaces. In various embodiments the external and internal stimulation material 822, 824 and/or sensors 830 can comprise various shapes, such as bands, rings, grids, dots, squares, rectangles, ovals, circles, ellipses, strips, stripes, matrices with appropriate spacing and insulation between layers or between electrodes to function properly for the desired effect. Any of the sensors or stimulators can be connected to one, two, three, four, five or more, ten or more, fifty or more, or one hundred or more, and any number of elements. Any one, or plurality of elements in the stimulators can be grouped. The sensors and/or stimulators can be configured to map the surface of the penis or the exterior surface of the therapeutic condom 800 in order to correlate sensations from one location to another. In other embodiments, the grid of stimulators can use pre-programmed stimulation patterns as communicated from a controller or microprocessor, through the device and/or through an external computer or wireless communication system. In various embodiments, controller 850 can be same or similar to controller 118, which is described above. In one embodiment controller 850 can include a microprocessor, like microprocessor 120.

In one embodiment controller 850 collects data from the sensors 830. In various embodiments controller 850 can collect, store and/or transmit data relating to stimulation sensed by the user, stimulation desired or set by the user, moving pattern, amplitude, speed, degree of stimulation, etc. In one embodiment controller 850 is multi-channeled (e.g. two, three, four or more channels) that are electrically isolated and independent. In one embodiment controller 850 has an ability of producing stimulation patterns with varying and different length, intensity, cycles, pattern, pulse duration, pulse rates, and/or frequency of stimulation and other characteristics.

Figure 9:
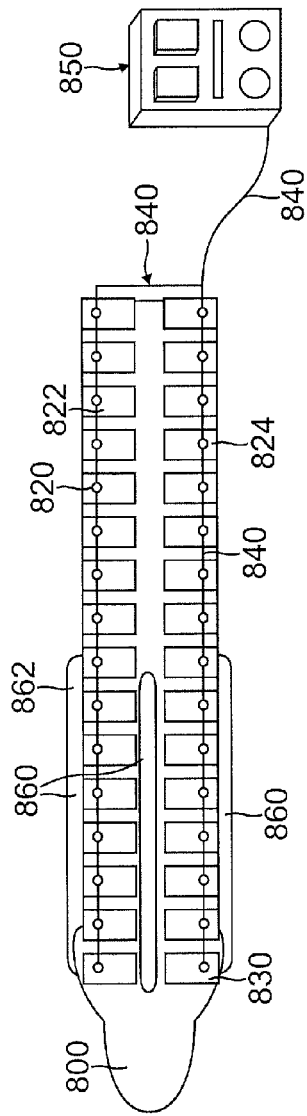
FIG. 9 is a schematic side view of a stimulating condom embodiment of a therapeutic prosthetic device with a reservoir.
Figure 10:
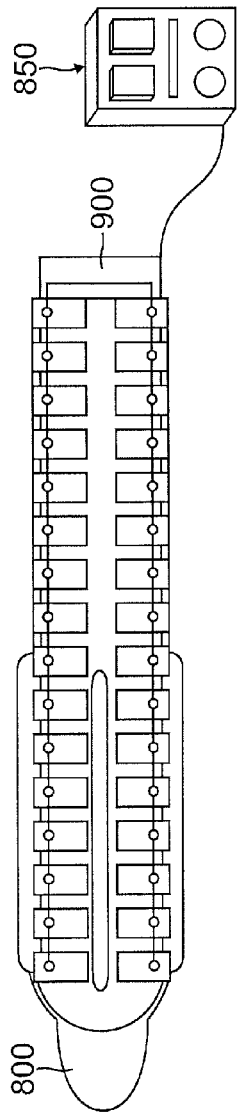
FIG. 10 is a schematic side view of the stimulating condom embodiment of FIG. 9 with a therapeutic prosthetic device with a reservoir on a penis.
Figure 13:
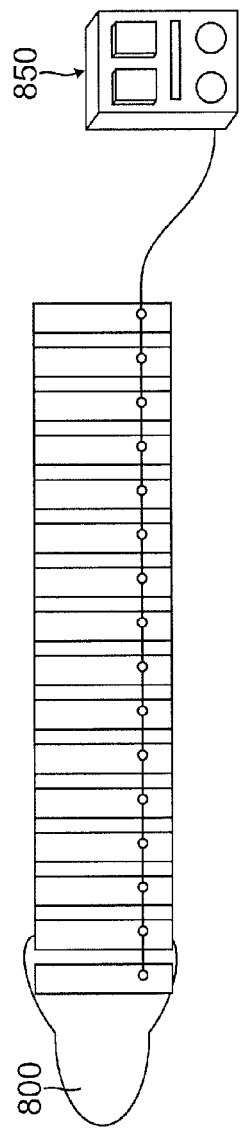
FIG. 13 is a schematic side view of a stimulating condom embodiment of a therapeutic prosthetic device.
Figure 14:
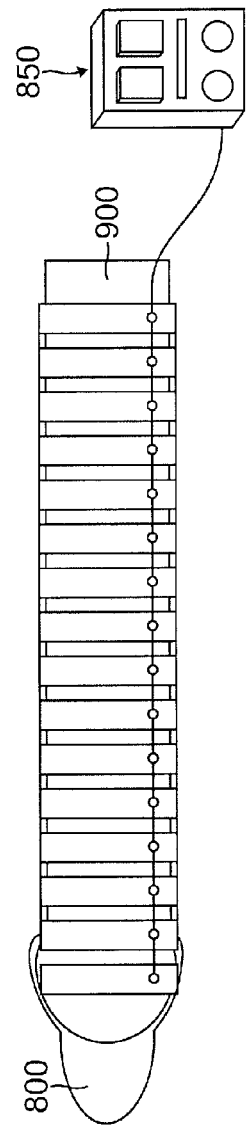
FIG. 14 is a schematic side view of the stimulating condom embodiment of FIG. 13 with a therapeutic prosthetic device on a penis.
Figure 15:
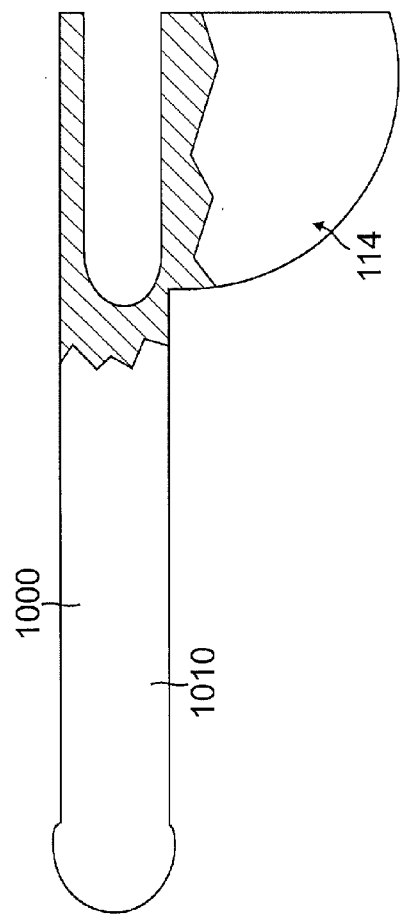
FIG. 15 is a schematic partial cross-sectional side view of a one embodiment of a unitary therapeutic prosthetic device with a bag.
Figure 16:
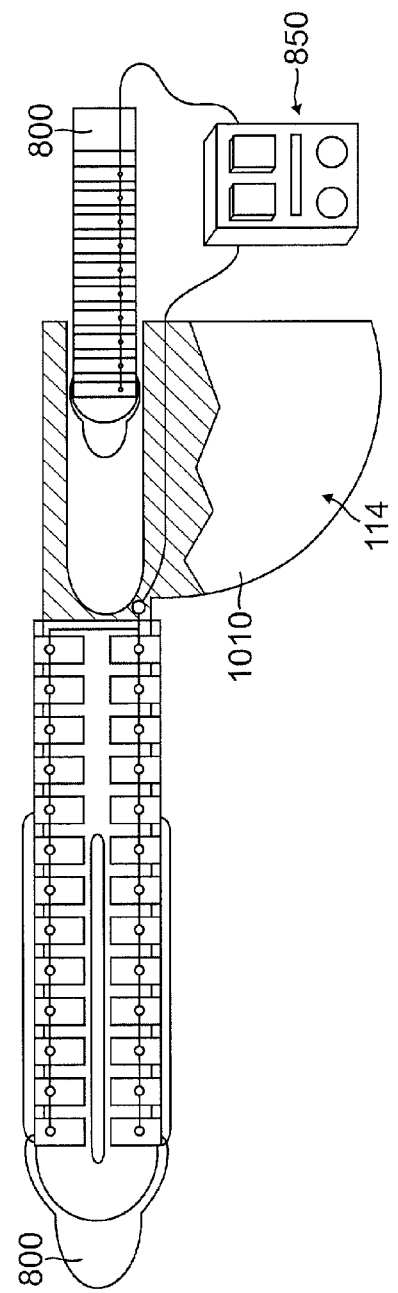
FIG. 16 is a schematic side view of the unitary therapeutic prosthetic device of FIG. 15 with embodiments of stimulation condoms.

In one embodiment the therapeutic condom can include one or more reservoirs 860. In one embodiment reservoir 860 is any reservoir 122 or 124. Reservoir 860 can be configured to deliver any media, such as a fluid, to the inside or outside of the therapeutic condom for release in an orifice or on the penis. In various embodiments reservoir 860 can contain lubricant, drugs, hormones, semen, or any type of fluid to be delivered to a bodily cavity, such as the vagina. For example, in one embodiment reservoir 860 is a fluid bladder containing a fluid which can be heated with heating element to deliver the fluid at, near, or above body temperatures through a port (not illustrated) to the orifice or penis. The fluid can be configured to simulate semen being ejaculated from the reservoir by a controller, and can be configured to correspond to actual ejaculation or orgasm in one or both of the sexual partners. In another embodiment, the fluid can be viable semen for insemination or impregnation purposes. In one embodiment, the reservoir 860 can be used to collect fluids or samples or take measurements of temperature, pH or other characteristics from the body cavity, such as a vagina. In one embodiment reservoir 860 can be inflated to change the size of the therapeutic condom 800 in any number of dimensions, including but not limited to diameter, width, length, girth, taper, ripple features, etc. In one embodiment reservoir 860 is a side reservoir 862, such as is illustrated in FIGS. 9 and 10. In one embodiment reservoir 860 is a tip reservoir 864, such as is illustrated in FIGS. 11 and 12. FIGS. 10, 12 and 14 illustrate a penis 900 inside the therapeutic condom 800. Any of the reservoirs 860 embodiments can be one or a plurality of reservoirs directed to the inside, the outside, or both sides of the therapeutic condom 800. In one embodiment the reservoir 860 comprises one or more micro-reservoirs configured to burst or emit fluid through one or more ports at the appropriate temperature, speed, friction, impact, or electronically controlled signal. FIGS. 13 and 14 illustrate an embodiment of a therapeutic condom 800 with no reservoir.

In various embodiments a therapeutic condom 800 can be used between partners for intercourse. Referring to FIGS. 15-21, in various embodiments a prosthesis 1000 is used in conjunction with one or more therapeutic condoms 800. In embodiment a prosthesis 1000 is used to supplement or assist in the sensations of intercourse. In one embodiment prosthesis 1000 is configured with similar features as prosthesis 102. In one embodiment prosthesis 1000 is configured and shaped to resemble the look and feel of an erect penis. In one embodiment prosthesis 1000 is configured with a bag 114. The prosthesis 1000 can be made of any rigid or semi-rigid yet soft material such as plastic, glass, metal, wood, rubber, silicone, or the like. In various embodiments one or more controllers 850 is operatively connected to one, two, or more therapeutic condoms 800. Although illustrated external to prosthesis 1000 in FIG. 16, in one embodiment a controller 850 can be placed on or inside prosthesis 1000, in any portion, including the bag 114. In one embodiment illustrated at FIG. 18, a controller 850 is operatively connected to a prosthesis 1000, which is then in turn operatively connectable to one or more therapeutic condoms 800. In one embodiment illustrated at FIGS. 15 and 16, a prosthesis 1010 includes a bag 114. In another embodiment illustrated at FIGS. 17-19, a prosthesis 1020 does not have a bag 114. In various embodiments, one or more separate prostheses 1030, 1040 may be used in conjunction with one or more therapeutic condoms 800, as illustrated in FIGS. 20 and 21. In one embodiment prosthetic shaft 1030 is configured to operate with a therapeutic condom 800 for use in an orifice. In one embodiment a prosthetic cavity 1040 is configured to operate with a therapeutic condom 800 for use with a penis. In one embodiment, prosthetic shaft 1030 and prosthetic cavity 1040 can be used with one, two, or more therapeutic condoms 800 and can communicate signals and/or data between the respective therapeutic condoms 800.

In use, the various therapeutic prosthetic devices described herein can be used by males and/or females, and do not need to be limited to insertion into body cavities such as the vagina, anus, or mouth. The sensors can be configured to convey sensations from other body or non-body parts, such as hands or other tactile devices.

Although a few embodiments have been described in detail above, other modifications are possible. Other embodiments may be within the scope of the following claims. It will be understood that the foregoing is only illustrative of the principles of the invention, and that various modifications, alterations, and combinations can be made by those skilled in the art without departing from the scope and spirit of the invention. Accordingly, it is not intended that the invention be limited, except as by the appended claims.

What is claimed is:

1. A prosthetic vaginal therapy device, comprising:
    an elongate prosthetic body comprising an outer surface, the outer surface configured and shaped to resemble the look and feel of an erect penis the body including an inner cavity, and
    a stimulation unit comprising a sensor, a microprocessor, and stimulation material, the sensor integrated with the inner cavity of the elongate prosthetic body for sensing a movement, pressure and/or force in an activity approximating sexual sensations; the sensor configured to generate signals based upon such movement, pressure and/or force in an activity approximating sexual sensations, the microprocessor configured for receiving signals from the sensor, the microprocessor adapted to generate a signal intended to represent a sensation in an activity approximating sexual sensations; and the stimulation material covering at least a portion of the outer surface for receiving the signal and generating stimulation in response to the signal.

2. The prosthetic vaginal therapy device in accordance with claim 1, further comprising a controller configured to control the sensation.

3. The prosthetic vaginal therapy device in accordance with claim 1, wherein the unitary prosthetic body further comprises the inner cavity configured to sense an insertion sensation of movement of an elongate body part in the inner cavity and generate an external sensation corresponding to the sensation movement of the elongate body part in the inner cavity.

4. The prosthetic vaginal therapy device in accordance with claim 1, further comprising a fluid delivery mechanism configured to deliver a fluid to the outer surface of the elongate prosthetic body for placement in a vagina.

5. The prosthetic vaginal therapy device in accordance with claim 4, wherein the fluid is selected from a group consisting of a lubricant, gel, liquid, hormone, medication, and sperm.

6. A method of therapeutic treatment of a vagina, comprising:
    inserting an elongate prosthetic body in a vagina, the elongate prosthetic body comprising an outer surface, a sensor, a microprocessor an inner cavity, and stimulation material, the sensor integrated with the inner cavity of the elongate prosthetic body for sensing a movement, pressure and/or force of the prosthesis in an activity approximating sexual sensations; the sensor configured to generate signals based upon such movement, pressure and/or force in an activity approximating sexual sensations, the microprocessor configured for receiving signals from the sensor, the microprocessor adapted to generate a signal intended to represent a sensation in an activity approximating sexual sensations; and the stimulation material covering at least a portion of the outer surface for receiving the signal; and
    simulating sexual sensation by activating said stimulation material on the outer surface with said signal.

7. The method of therapeutic treatment of a vagina of claim 6, further comprising delivering a fluid from the elongate prosthetic body to the vagina.

8. The method of therapeutic treatment of a vagina of claim 7, wherein the fluid is selected from a group consisting of lubricant, gel, liquid, hormone, medication, and sperm.

* * * * *